(12) United States Patent
Yagi

(10) Patent No.: US 6,535,573 B2
(45) Date of Patent: Mar. 18, 2003

(54) X-RAY FLUORESCENCE ANALYZER

(75) Inventor: Shigeki Yagi, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/915,447

(22) Filed: Jul. 26, 2001

(65) Prior Publication Data

US 2002/0015471 A1 Feb. 7, 2002

(30) Foreign Application Priority Data

Jul. 27, 2000 (JP) ........................................ 2000-227377

(51) Int. Cl.$^7$ ............................................. G01N 23/223
(52) U.S. Cl. ........................................ 378/45; 378/206
(58) Field of Search ................................ 378/206, 45

(56) References Cited

U.S. PATENT DOCUMENTS 4,969,177 A * 11/1990 Otsubi ........................ 378/206

* cited by examiner

*Primary Examiner*—Craig E. Church
(74) *Attorney, Agent, or Firm*—Adams & Wilks

(57) ABSTRACT

Handling of a portable an X-ray fluorescence analyzer is simplified by providing in a housing of the X-ray fluorescence analyzer an X-ray source for irradiating primary X-rays onto a sample to be measured located outside the housing, and a light source in the housing for irradiating a visible light beam in the irradiating direction of the primary X-rays, the visible light beam having a different optical axis from the X-rays.

15 Claims, 2 Drawing Sheets

X-RAY FLUORESCENCE ANALYZER

BACKGROUND OF THE INVENTION

The present invention relates to an X-ray fluorescence analyzer, having a system of irradiating primary X-rays onto a sample to be measured located outside of the apparatus, such as a portable X-ray fluorescence analyzer mainly aimed at outdoor elementary analysis, such as archaeological sample examination, criminal field searches, and initial stages of fire investigations.

In a typical X-ray fluorescence analyzer, because an object to be measured can be included inside the structural body of a sealed type sample chamber, protection against X-ray leakage to the outside of an apparatus can be easily carried out using a safety interlocking method by detecting a condition of the sample chamber door. On the other hand, in a portable X-ray fluorescence analyzer used in many cases at unspecified locations such as outdoors, primary X-rays may be irradiated onto a sample to be measured located outside of the apparatus. In this case, as X-ray irradiation becomes completely open to the direction of the object to be measured, a complicated safety interlocking method is needed in order to secure the safety of a measurer and people around the X-ray fluorescence analyzer. For example, as disclosed in Japanese Patent laid open No. Hei. 11-304733, both a measuring unit housing and a handle unit of an X-ray fluorescence analyzer have a micro switch, as well as having safety interlocking means where X-rays are only generated when the former micro switch is on and the latter is off, in other words, when an X-ray shutter is in open condition.

According to the safety interlocking method as disclosed in Japanese Patent laid open No. Hei. 11-304733, the safety of the measurer and the people around the X-ray fluorescence analyzer can be maintained. However, in this case, it is necessary to adjust locations of a sample to be measured and a measuring unit of the analyzer so that the micro switch attached to the measuring unit housing of the analyzer becomes on during measurement, and in many cases, it takes time for installation operations. If X-rays were visible, it would be easy for the measurer and the people around the X-ray fluorescence analyzer to protect against exposure. However, since X-rays are not visible on observation side, there is no alternative but to take this option even at the risk of sacrificing simple and easy handling. This invention has as its object to provide an X-ray fluorescence analyzer having simple handling, to solve the above described problems.

SUMMARY OF THE INVENTION

In order to resolve the above problems, an X-ray fluorescence analyzer of this invention is provided with a light source placed in the analyzer housing so that a light beam is irradiated in the irradiating direction of X-rays during measurement, namely during irradiation of primary X-rays.

When the measurer instructs measurement start, one or more light beams visible on the observation side travel in the irradiating direction of primary X-rays. These light beams visually notify the measurer and other people around the analyzer that the area surrounding the moving light beams has become an electromagnetically dangerous spot.

DETAILED DESCRIPTION OF THE PREFERRED EMBODIMENT

Embodiments of the present invention will be described in the following based on the drawings.

(1) First Embodiment

Figure 1:
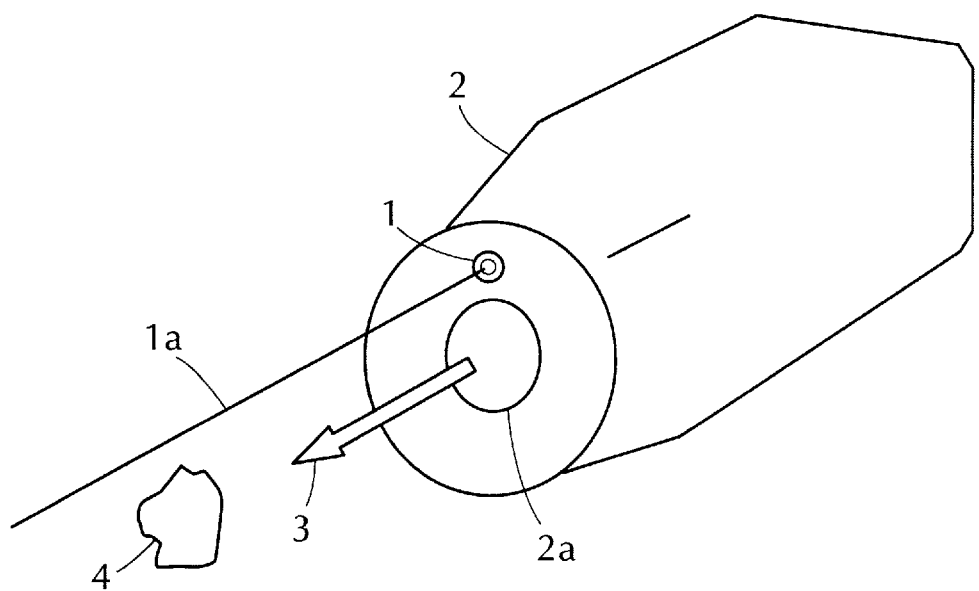
FIG. 1 shows a configuration of an X-ray fluorescence analyzer of the present invention.
Figure 2:
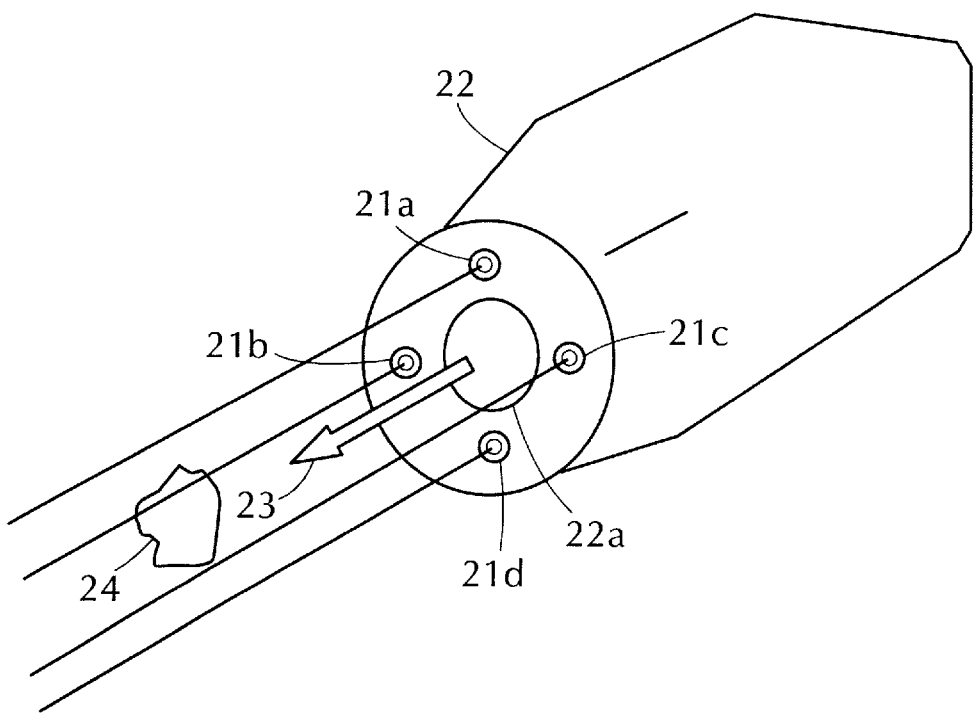
FIG. 2 shows a second embodiment of the X-ray fluorescence analyzer of the present invention.

FIG. 1 is a block diagram of the present invention showing the condition of an X-ray fluorescence analyzer at the instant of implementing measurement. One light source 1 is provided in the vicinity of an X-ray irradiating opening 2a of an analyzer housing 2. Here, a small laser oscillating unit is used as a light source. When measurement start is instructed, primary X-rays are irradiated from the X-ray irradiating opening 2a to a sample to be measured 4. At the same time, a laser is irradiated from the small laser oscillating unit 1. A laser emission line 1a is observed in the same direction of a primary X-ray beam 3. People around the analyzer, including the measurer, are visually notified that space surrounding the laser emission line 1a has become an electromagnetically dangerous spot, and are made wary. The laser used in the first embodiment is essentially a safe or low power product equal to or lower than 1 mW, and so safety is reliably secured. When using a laser, a clear emission line can be obtained. When measurement end is instructed and irradiation of primary X-rays is stopped, the irradiation of the laser is also stopped, (2) Second Embodiment The second embodiment of FIG. 2 shows that 4 small laser oscillating units 21a, 21b, 21c, and 21d are provided around an X-ray irradiating opening 22a of an analyzer housing 22. When measurement start is instructed, primary X-rays are irradiated from the X-ray irradiating opening 22a to a sample to be measured 24. At the same time, lasers are irradiated from the small laser oscillating units 21a, 21b, 21c, and 21d. 4 laser emission lines are irradiated in the same direction as a primary X-ray beam 23, as well as surrounding the primary X-ray beam 23 as a center. People around the analyzer, including the measurer, are visually notified that the space surrounding the laser emission line has become an electromagnetically dangerous spot, and are made wary. If a plurality of emission lines exist, it is possible to give the impression of a dangerous space over a wide range. The laser used in the second embodiment is one securing reliable safety, the same as the laser used in the first embodiment. When measurement end is instructed and irradiation of primary X-rays is stopped, the irradiation of the laser is also stopped.

(3) Third Embodiment

Figure 3:
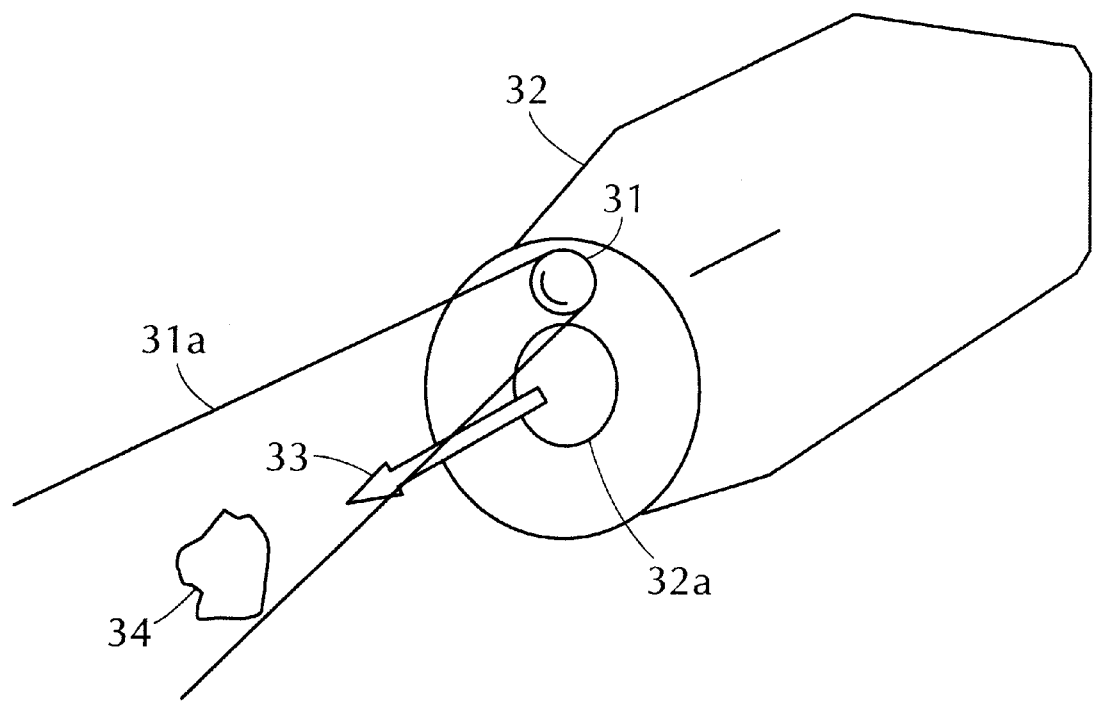
FIG. 3 shows a third embodiment of the X-ray fluorescence analyzer of the present invention.

The third embodiment of FIG. 3 shows that one lighting unit 31 is provided in the vicinity of an X-ray irradiating opening 32a of an analyzer housing 32. This lighting unit comprises, for instance, a bulb and a lens, and can generate beams having directivity. When measurement start is instructed, primary X-rays are irradiated from the X-ray irradiating opening 32a to a sample to be measured 34. At this time, a light beam 31a from the lighting unit 31 is generated. The light beam 31a is generated in the same direction as a primary X-ray beam 33. People around the analyzer, including the measurer, are visually notified that the space surrounding the light beam 31a has become an electromagnetically dangerous spot, and are made wary. It is possible to construct the lighting unit inexpensively. In addition, as the light beam itself widens to a certain extent, it is possible to give the impression of a dangerous space over a wide range. When the color of the light beam is made red, it has high visibility and is good for attracting attention. When measurement end is instructed and irradiation of primary X-rays is stopped, the irradiation of light by the lighting unit is also stopped. An X-ray fluorescence analyzer of present invention, having a system of irradiating primary X-rays onto a sample to be measured located outside of the apparatus, utilizing principles of an X-ray fluorescence method, has a light source placed in the analyzer housing so that a light beam is irradiated in the irradiating direction of primary X-rays. In this way, people around the analyzer, including the measurer, are visually notified that space at the irradiating direction side of primary X-rays has become an electromagnetically dangerous spot, and are effectively made wary. Therefore, it is not necessary to carry out complicated procedures such as subtly adjusting locations of a sample to be measured and a measuring unit of the analyzer, thus making it possible to obtain an X-ray fluorescence analyzer that is easy to handle.

What is claimed is:

1. A portable X-ray fluorescence analyzer, comprising: a housing; an X-ray source disposed in the housing for irradiating a primary X-ray beam through a first opening in the housing and onto a sample located outside of the housing for analysis of the sample utilizing principles of X-ray fluorescence; a light source disposed in the housing for irradiating a visible light beam through a second opening in the housing and in the irradiating direction of the primary X-ray beam and means for activating said light source only when the primary X-ray beam is being irradiated, an axis of the visible light beam being different from that of the primary X-ray beam.

2. A portable X-ray fluorescence analyzer according to claim 1; wherein the first opening is spaced apart from the second opening, and the first and second openings are formed in a side of the housing.

3. A portable X-ray fluorescence analyzer according to claim 1; wherein the light source comprises a low power laser source having a power no greater than 1 mW.

4. A portable X-ray fluorescence analyzer according to claim 1; wherein the light source comprises a bulb and a lens for producing a beam having directivity.

5. A portable X-ray fluorescence analyzer according to claim 1; further comprising one or more other visible light sources disposed in the housing for irradiating visible light beams through respective openings in the housing and in the irradiating direction of the primary X-ray beam, an axis of the visible light beams being different from that of the primary X-ray beam.

6. A portable X-ray fluorescence analyzer according to claim 5; wherein the openings corresponding to the respective light sources are disposed about a periphery of the first opening corresponding to the X-ray source.

7. A portable X-ray fluorescence analyzer according to claim 5; wherein the other light sources comprise low power laser sources having a power no greater than 1 mW.

8. A portable X-ray fluorescence analyzer according to claim 1; wherein the visible light beam is red.

9. A portable X-ray irradiation apparatus comprising: a housing; an X-ray source disposed in the housing for irradiating an X-ray beam in an irradiating direction onto a sample located outside of the housing; one or more light sources disposed in the housing for irradiating visible light beams in the irradiating direction of the X-ray beam and means for activating the one or more light sources only when the X-ray beam is being irradiated; wherein axes of the visible light beams are not coaxial with an axis of the X-ray beam.

10. An X-ray irradiation apparatus according to claim 9; wherein the visible light beams are red light beams.

11. An X-ray irradiation apparatus according to claim 9; wherein the X-ray beam is irradiated through a first opening in the housing.

12. An X-ray irradiation apparatus according to claim 11; wherein the visible light beams are irradiated through openings in the housing spaced apart from each other and spaced apart from the first opening.

13. An X-ray irradiation apparatus according to claim 9; wherein the one or more light sources comprise low power laser sources having a power no greater than 1 mW.

14. An X-ray irradiation apparatus according to claim 9; wherein the one or more light sources each comprise a bulb and a lens for producing a beam having directivity.

15. An X-ray irradiation apparatus according to claim 9; wherein openings in the housing for projecting the visible light beams are disposed about a periphery of an opening in the housing for projecting the X-ray beam.

* * * * *